United States Patent
Lin et al.

(10) Patent No.: US 10,456,084 B1
(45) Date of Patent: Oct. 29, 2019

(54) INTELLIGENT HOSPITAL BED

(71) Applicants: Yao-Sheng Lin, Changhua (TW);
Tsair-Rong Chen, Changhua (TW);
Yu-Lin Juan, Changhua (TW)

(72) Inventors: Yao-Sheng Lin, Changhua (TW);
Tsair-Rong Chen, Changhua (TW);
Yu-Lin Juan, Changhua (TW)

(73) Assignees: Yung Hsiang Information Management, Co. Ltd, Cganghua (TW); Dept. of Electrical Engineering, National Changhua University of Education, Changhua (TW)

( * ) Notice: Subject to any disclaimer, the term of this patent is extended or adjusted under 35 U.S.C. 154(b) by 0 days.

(21) Appl. No.: 16/053,632

(22) Filed: Aug. 2, 2018

(51) Int. Cl.
| | |
|---|---|
| *G08B 23/00* | (2006.01) |
| *A61B 5/00* | (2006.01) |
| *A61M 5/14* | (2006.01) |
| *A61B 5/20* | (2006.01) |
| *A61M 5/168* | (2006.01) |
| *A61G 7/05* | (2006.01) |
| *G16H 40/63* | (2018.01) |
| *G16H 20/17* | (2018.01) |

(52) U.S. Cl.
CPC .......... *A61B 5/6892* (2013.01); *A61B 5/0002* (2013.01); *A61B 5/208* (2013.01); *A61G 7/0503* (2013.01); *A61G 7/0527* (2016.11); *A61M 5/1415* (2013.01); *A61M 5/16845* (2013.01); *G16H 20/17* (2018.01); *G16H 40/63* (2018.01); *A61B 2562/0247* (2013.01); *A61M 2205/3306* (2013.01)

(58) Field of Classification Search
CPC ..... A61B 5/6892; A61B 5/0002; A61B 5/208; A61B 2562/0247; A61G 7/0527; A61G 7/0503; G16H 20/17; G16H 40/63; A61M 5/1415; A61M 5/16845; A61M 2205/3306
USPC ...................................... 340/573.1
See application file for complete search history.

(56) References Cited

U.S. PATENT DOCUMENTS

| | | | | |
|---|---|---|---|---|
| 7,652,581 | B2 * | 1/2010 | Gentry | A61B 5/11 340/573.1 |
| 9,271,665 | B2 * | 3/2016 | Sarrafzadeh | G01L 1/18 |
| 9,492,341 | B2 * | 11/2016 | Huster | A61B 5/1115 |
| 2004/0189475 | A1 * | 9/2004 | Cooper | A61B 5/1118 340/573.1 |
| 2005/0165325 | A1 * | 7/2005 | Hornig | A61G 7/05 600/549 |

(Continued)

*Primary Examiner* — Zhen Y Wu
(74) *Attorney, Agent, or Firm* — Che-Yang Chen; Law Offices of Scott Warmuth (57) ABSTRACT

An intelligent hospital bed may comprise a hospital bed, a first measuring unit, at least a second measuring unit, a third measuring unit, a central processor and a remote transmission device. The central processor is configured to receive signals from the measuring units and interpret the signals through comparison of data in a database of the central processor or a server. After interpreting, the central processor is configured to connect to the remote transmission device and send the interpreted information to a human-computer interaction through the remote transmission device such that the caregiver is able to master real-time conditions of patients respectively in the hospital beds including injection and urination status at the same time, thereby achieving the most effective allocation and utilization of care resource.

10 Claims, 8 Drawing Sheets

(56) References Cited

U.S. PATENT DOCUMENTS

| | | | |
|---|---|---|---|
| 2008/0035156 A1* | 2/2008 | Hyde | A61F 5/05 |
| | | | 128/845 |
| 2008/0147442 A1* | 6/2008 | Warner | A61G 7/018 |
| | | | 705/3 |
| 2012/0089419 A1* | 4/2012 | Huster | A61B 5/1115 |
| | | | 705/3 |
| 2012/0248181 A1* | 10/2012 | Zerhusen | G06F 19/3418 |
| | | | 235/375 |
| 2013/0298330 A1* | 11/2013 | Lachenbruch | A61G 7/057 |
| | | | 5/606 |
| 2014/0259406 A1* | 9/2014 | Ead | A47C 21/028 |
| | | | 5/488 |
| 2015/0109442 A1* | 4/2015 | Derenne | G06F 16/78 |
| | | | 348/143 |
| 2015/0135436 A1* | 5/2015 | Stryker | A61G 7/05 |
| | | | 5/600 |
| 2016/0136024 A1* | 5/2016 | Poenisch | B25J 21/02 |
| | | | 600/21 |
| 2016/0314270 A1* | 10/2016 | Hsu | G06F 19/3418 |
| 2017/0055917 A1* | 3/2017 | Stone | A61B 5/7275 |
| 2017/0238827 A1* | 8/2017 | Seba | A61B 5/6892 |
| 2018/0064594 A1* | 3/2018 | Finch, Jr. | A61G 7/05784 |
| 2018/0317841 A1* | 11/2018 | Novak, Jr. | A61B 5/4839 |
| 2018/0338806 A1* | 11/2018 | Grubbs | A61B 34/30 |

\* cited by examiner

INTELLIGENT HOSPITAL BED

FIELD OF THE INVENTION

The present invention relates to a hospital bed and more particularly to an intelligent hospital bed adapted to monitor the status of patient.

BACKGROUND OF THE INVENTION

Nowadays, the progress of modern medical technologies have effectively and significantly prolonged the life of human. However, in the same time, it means that the proportion of medical practices need to be increased. Patents always need to stay in hospital bed for treatment or hospitalization when facing serous or complex illness, and for those serious patients who are unable to take care of their own lives, they always rely on the caregiver assisting in the care of daily living such as excretion, eating, bathing, and having intravenous drip.

However, the conventional medical care is not yet perfected because: a caregiver in the hospital always need to be responsible for taking care of multiple patients, and the large medical population in today may result in a lack of resource for comprehensive cares, thereby seriously affecting the quality of medical care and causing medical disputes. Therefore, there remains a need for a new and improved design for an intelligent hospital bed to overcome the problems presented above.

SUMMARY OF THE INVENTION

The present invention provides an intelligent hospital bed which comprises a hospital bed, a first measuring unit, at least a second measuring unit, a third measuring unit, a central processor and a remote transmission device. The first measuring unit is a pad body having a pressure sensor, and the first measuring unit is installed on the hospital bed. When a patient lies on the hospital bed, the pressure sensor of the first measuring unit is configured to measure the pressure and send a first signal to the central processor which is adapted to determine whether the patient lies on the hospital bed as instructed, thereby preventing the patient from leaving the hospital bed by himself/herself. The second measuring unit is adapted to measure the use status of an IV bag hanged on an IV stand near the hospital bed, and the second measuring unit is adapted to measure the IV use status and send a second signal to the central processor which is configured to determine whether the intravenous drip is successful used and to have immediately report for remaining amount of drip in the IV bag after each use. The third measuring unit is configured to measure the urination condition of a patient and send a third signal to the central processor. The central processor is configured to receive the signals from the measuring units and interpret the signals through comparison of data in a database of the central processor or a server. After interpreting, the central processor is configured to connect to the remote transmission device and send the interpreted information to a human-computer interaction through the remote transmission device such that the caregiver is able to master real-time conditions of patients respectively in the hospital beds including injection and urination status at the same time, thereby achieving the most effective allocation and utilization of care resource.

Comparing with conventional hospital bed, the present invention is advantageous because: (i) the signals measured from the measuring units are configured to send to central processor, and the central processor is adapted to interpret the signals and send the interpreted information to the human-computer interaction through the remote transmission device such that the caregiver is able to master real-time conditions of patients respectively in the hospital beds including injection and urination status at the same time, thereby achieving the most effective allocation and utilization of care resource; and (ii) the caregiver is configured to receive alert from the human-computer interaction when the patient leaves the hospital bed or the intravenous drip of the patient needs to be replaced.

DETAILED DESCRIPTION OF THE INVENTION

The detailed description set forth below is intended as a description of the presently exemplary device provided in accordance with aspects of the present invention and is not intended to represent the only forms in which the present invention may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described can be used in the practice or testing of the invention, the exemplary methods, devices and materials are now described.

All publications mentioned are incorporated by reference for the purpose of describing and disclosing, for example, the designs and methodologies that are described in the publications that might be used in connection with the presently described invention. The publications listed or discussed above, below and throughout the text are provided solely for their disclosure prior to the filing date of the present application. Nothing herein is to be construed as an admission that the inventors are not entitled to antedate such disclosure by virtue of prior invention.

In order to further understand the goal, characteristics and effect of the present invention, a number of embodiments along with the drawings are illustrated as following:

Referring to FIGS. 1 to 6, the present invention provides an intelligent hospital bed which comprises a hospital bed (10), a first measuring unit (20), at least a second measuring unit (30), a third measuring unit (40), a central processor (50) and a remote transmission device (60). The first measuring unit (20) is a pad body having a pressure sensor, and the first measuring unit (20) is installed on the hospital bed (10). When a patient lies on the hospital bed (10), the pressure sensor of the first measuring unit (20) is configured to measure the pressure and send a first signal (201) to the central processor (50) which is adapted to determine whether the patient lies on the hospital bed (10) as instructed, thereby preventing the patient from leaving the hospital bed (10) by himself/herself. The second measuring unit (30) is adapted to measure the use status of an intravenous (IV) bag (71) hanged on an IV stand (70) near the hospital bed (10), and the second measuring unit (30) is adapted to measure the IV use status and send a second signal (301) to the central processor (50) which is configured to determine whether the intravenous drip is successful used and to have immediately report for remaining amount of drip in the IV bag (71) after each use. The third measuring unit (40) is configured to measure the urination condition of a patient and send a third signal (401) to the central processor (50). The central processor (50) is configured to receive the signals (201)(301)(401) from the measuring units (20)(30)(40) and interpret the signals (201)(301)(401) through comparison of data in a database of the central processor (50) or a server. After interpreting, the central processor (50) is configured to connect to the remote transmission device (60) and send the interpreted information to a human-computer interaction (80) through the remote transmission device (60) such that the caregiver is able to master real-time conditions of patients respectively in the hospital beds (10) including injection and urination status at the same time, thereby achieving the most effective allocation and utilization of care resource.

In one embodiment, the second measuring unit (30) is a camera (31) which is configured for fixed-position photography to determine the liquid level in the IV bag (71) (as shown in FIGS. 1 to 6).

In another embodiment, the second measuring unit (30) is a focal-length-adjustable and optical-zoom camera (31), and the camera (31) is configured to be timed or manually remote controlled to turn to an designed angle and back so as to monitor the liquid level in the IV bag (71) and to monitor around the hospital bed (10), thereby enabling the caregiver to well control the immediate status of a patient lying on the hospital bed (10).

Figure 7:
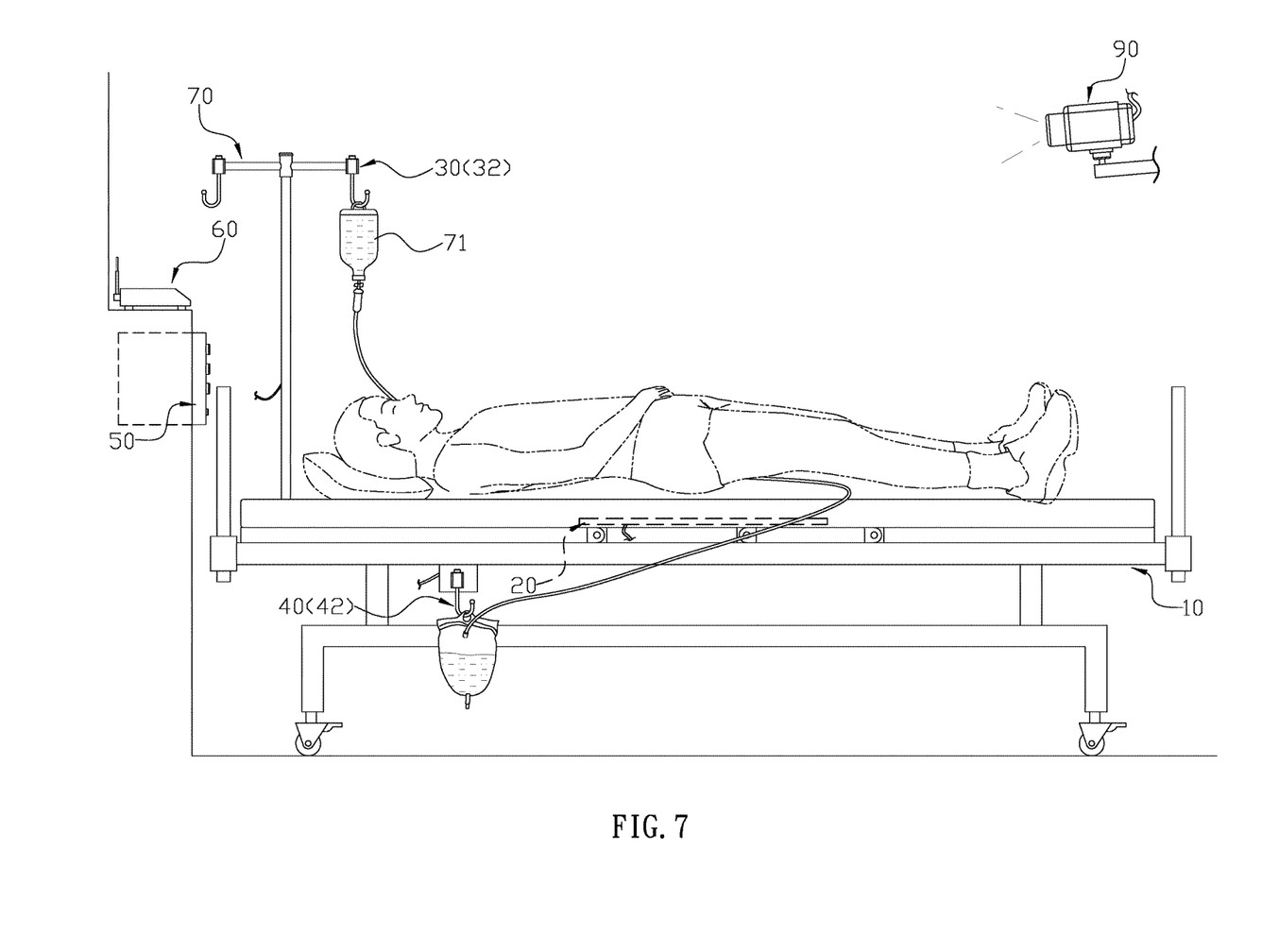
FIG. 7 is a plan view of another embodiment of the intelligent hospital bed of the present invention.
Figure 8:
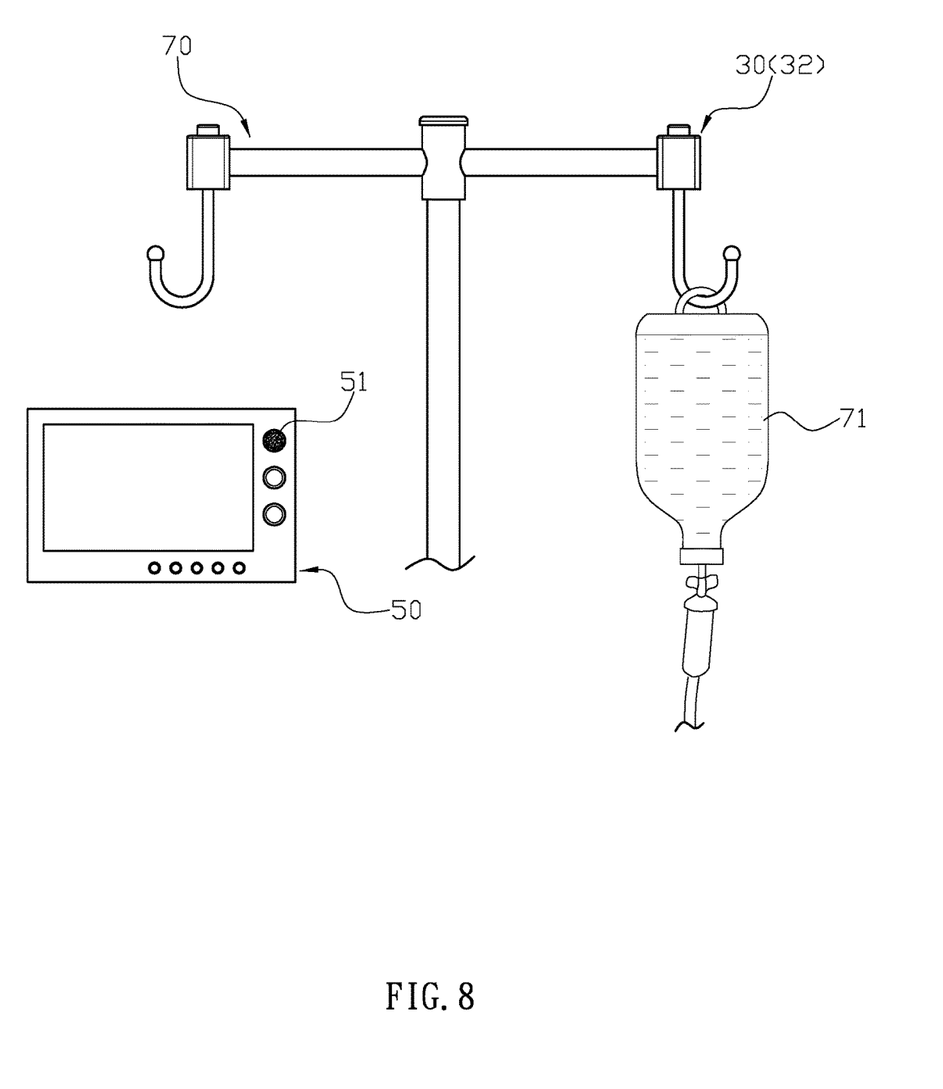
FIG. 8 is a deployment diagram of another embodiment of the second measuring unit of the intelligent hospital bed in the present invention.

In still another embodiment, the second measuring unit (30) installed on the IV stand (70) comprises a crane scale (32), and the IV bag (71) is hung on the crane scale (32) so as to enable the crane scale (32) to measure the weight of the IV bag (71) at any time, thereby fully mastering the use status of the intravenous drip (as shown in FIGS. 7 and 8).

Figure 1:
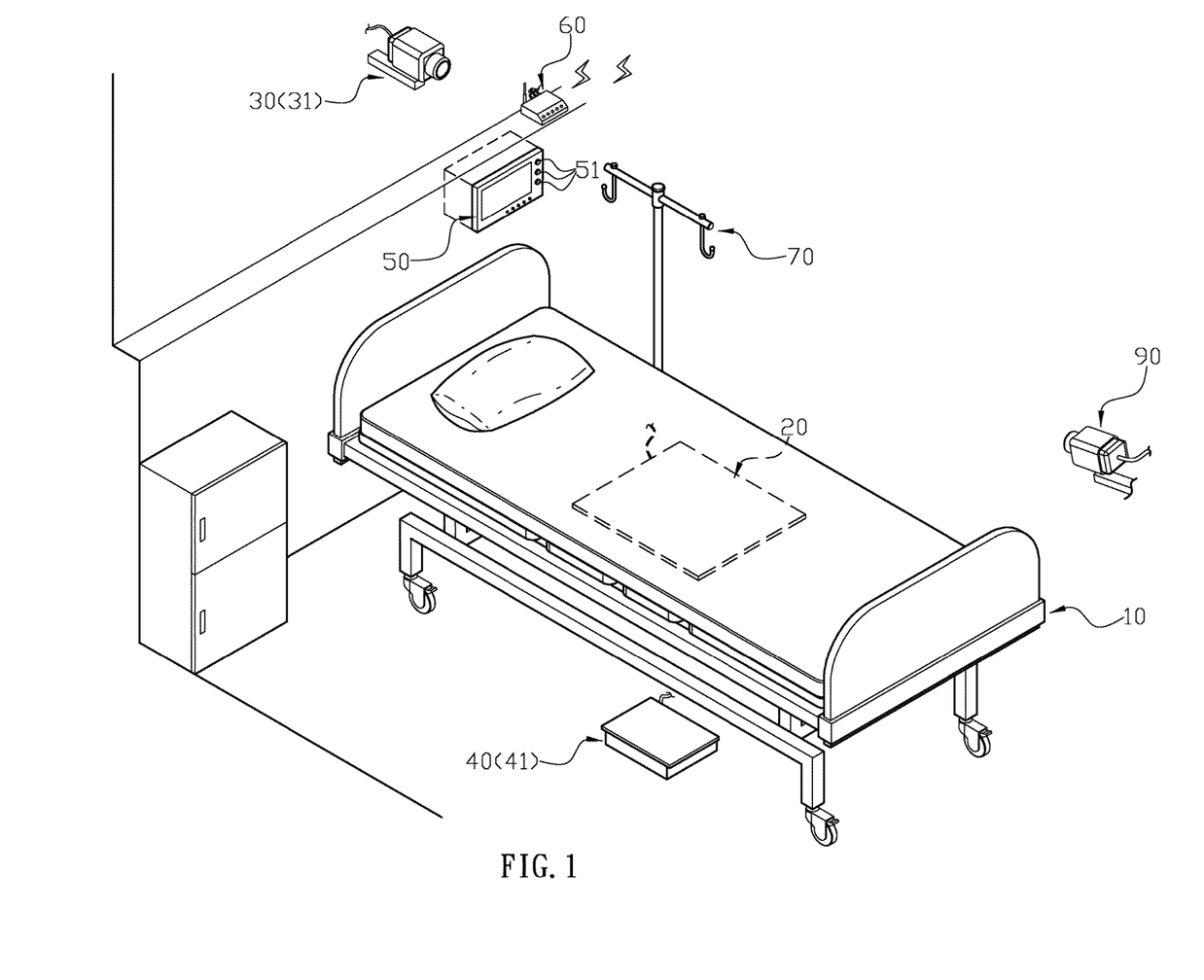
FIG. 1 is a three-dimensional assembly view of an intelligent hospital bed of the present invention.
Figure 2:
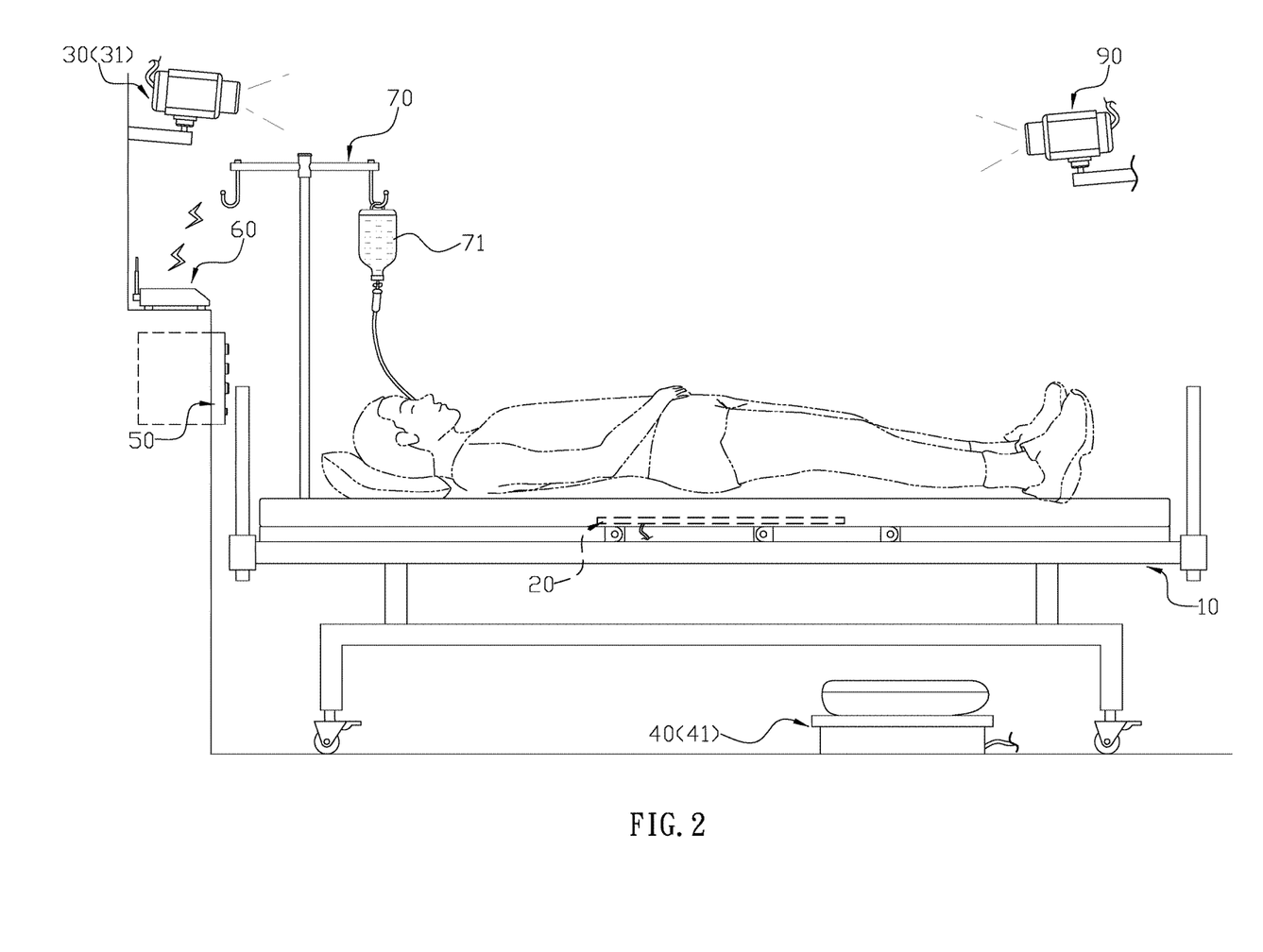
FIG. 2 is a plan view of the intelligent hospital bed of the present invention.
Figure 3:
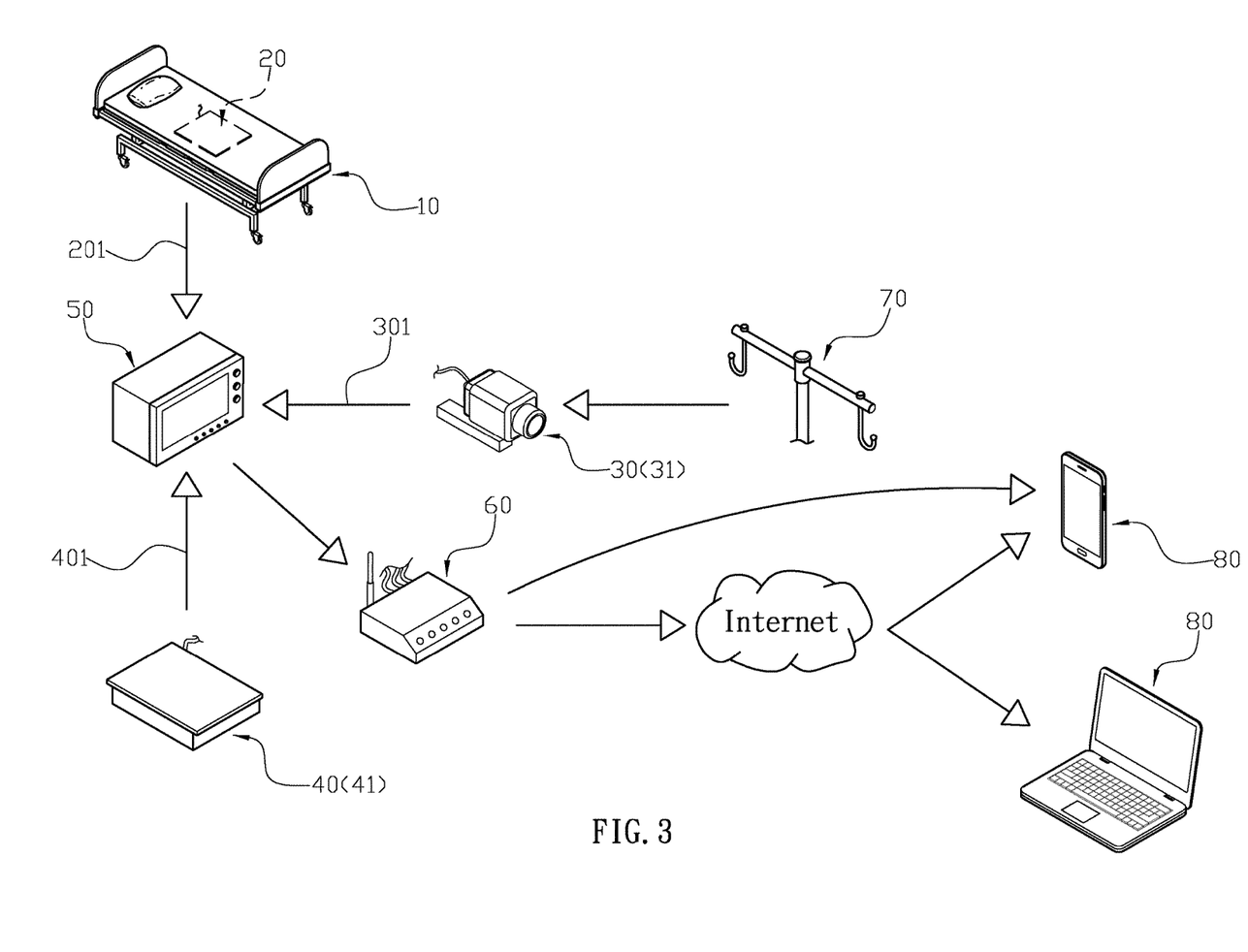
FIG. 3 is an integral frame diagram of the intelligent hospital bed of the present invention.

In a further embodiment, the third measuring unit (40) is a weighing platform (41) which enables a urinal pot to be put thereon (as shown in FIGS. 1 to 3), and the weighting platform (41) is configured to measure the weight of the urinal pot at any time, thereby fulling mastering the urination condition of a patient.

In still a further embodiment, the third measuring unit (40) installed on the hospital bed (10) has a hanging scale (42) to hang a urinal bag thereon, and the hanging scale (42) is configured to measure the weight of the urinal bag at any time, thereby fulling mastering the urination condition of a patient (as shown in FIG. 7).

In yet a further embodiment, the central processor (50) is installed on a wall located near a head side of the hospital bed (10) (as shown in FIGS. 1 and 2).

In a particular embodiment, the central processor (50) is directly secured on the hospital bed (10).

Figure 4:
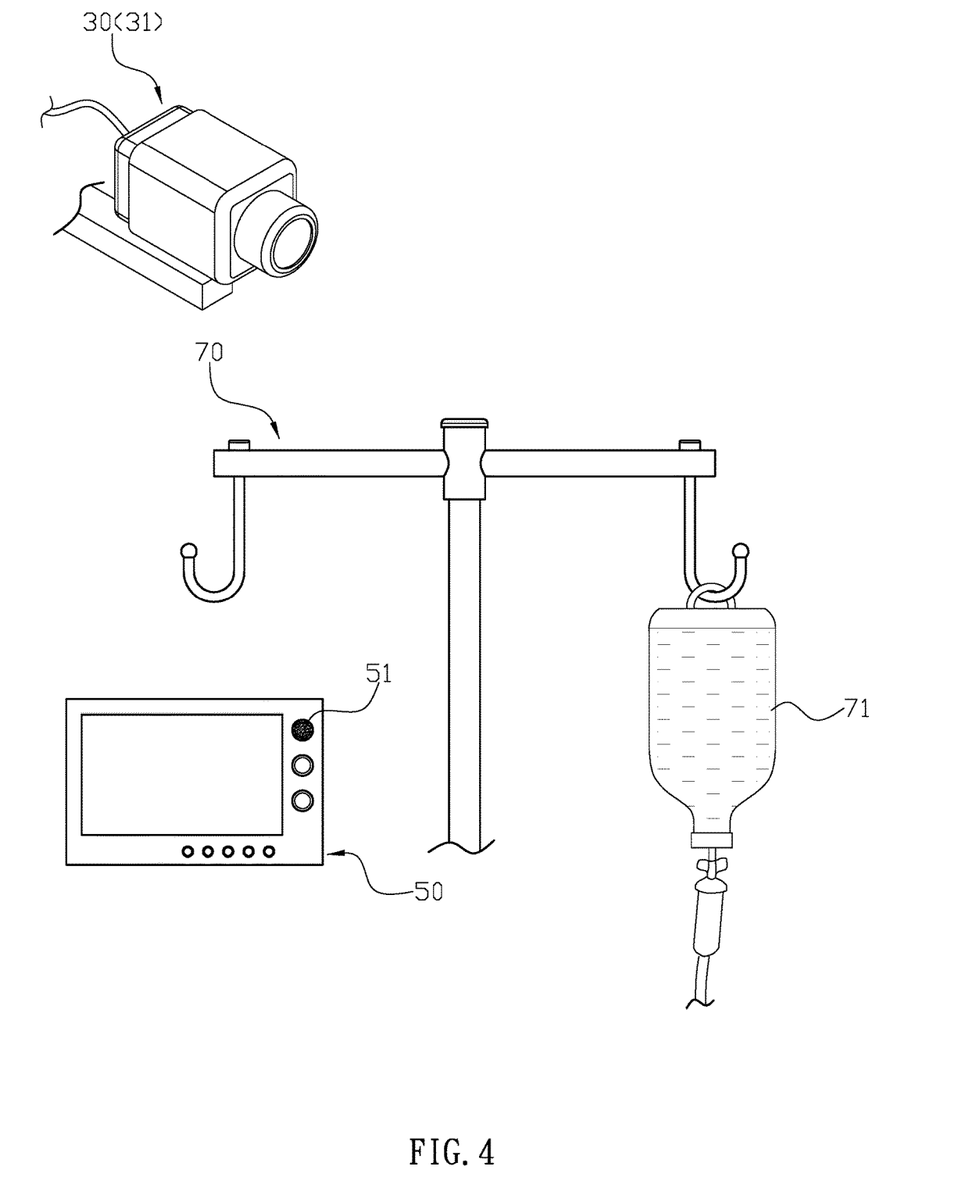
FIG. 4 is a schematic view illustrating the liquid level in an IV bag measured by a second measuring unit of the intelligent hospital bed is at high level in the present invention.
Figure 5:
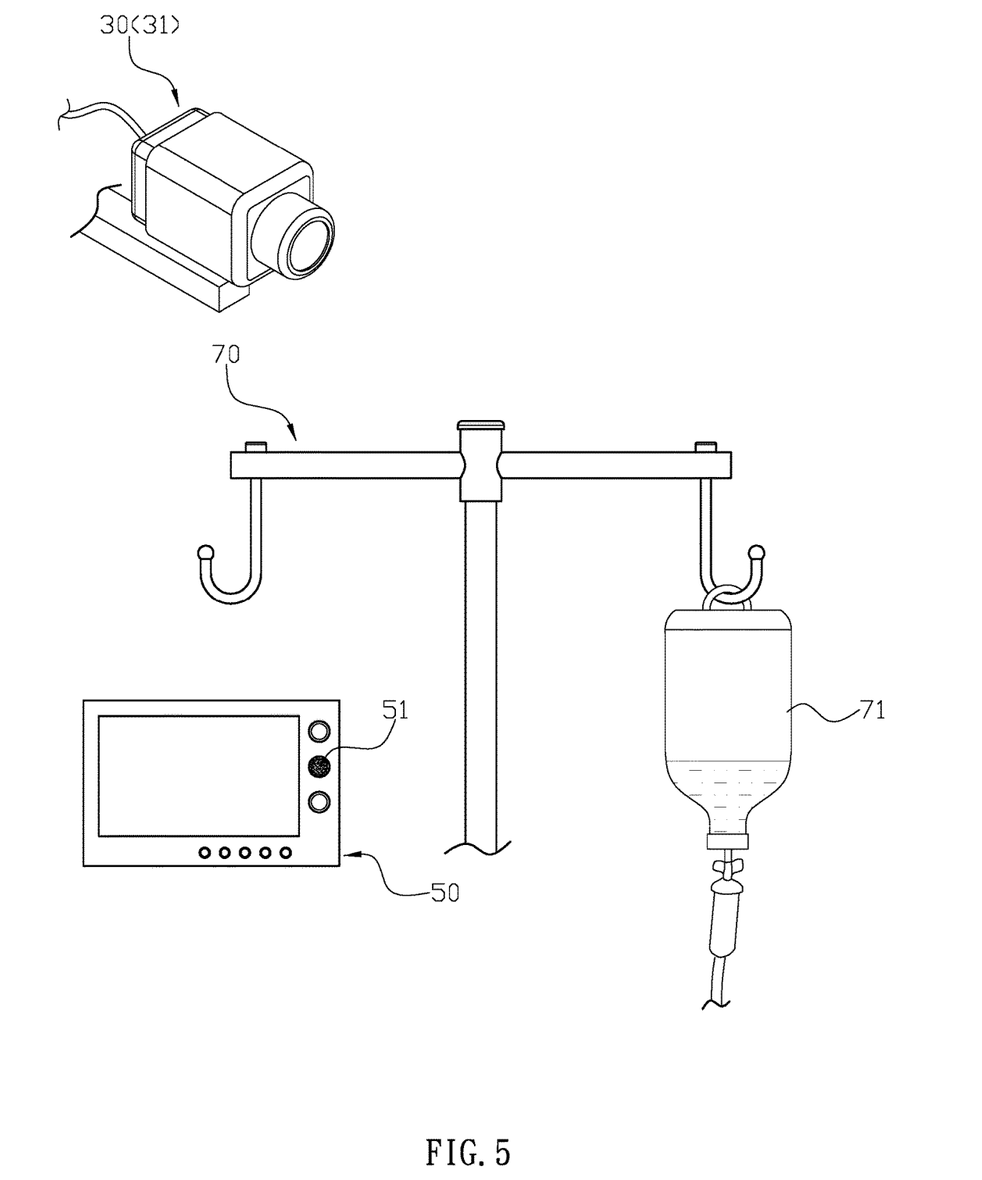
FIG. 5 is a schematic view illustrating the liquid level in the IV bag measured by the second measuring unit of the intelligent hospital bed is at middle level in the present invention.
Figure 6:
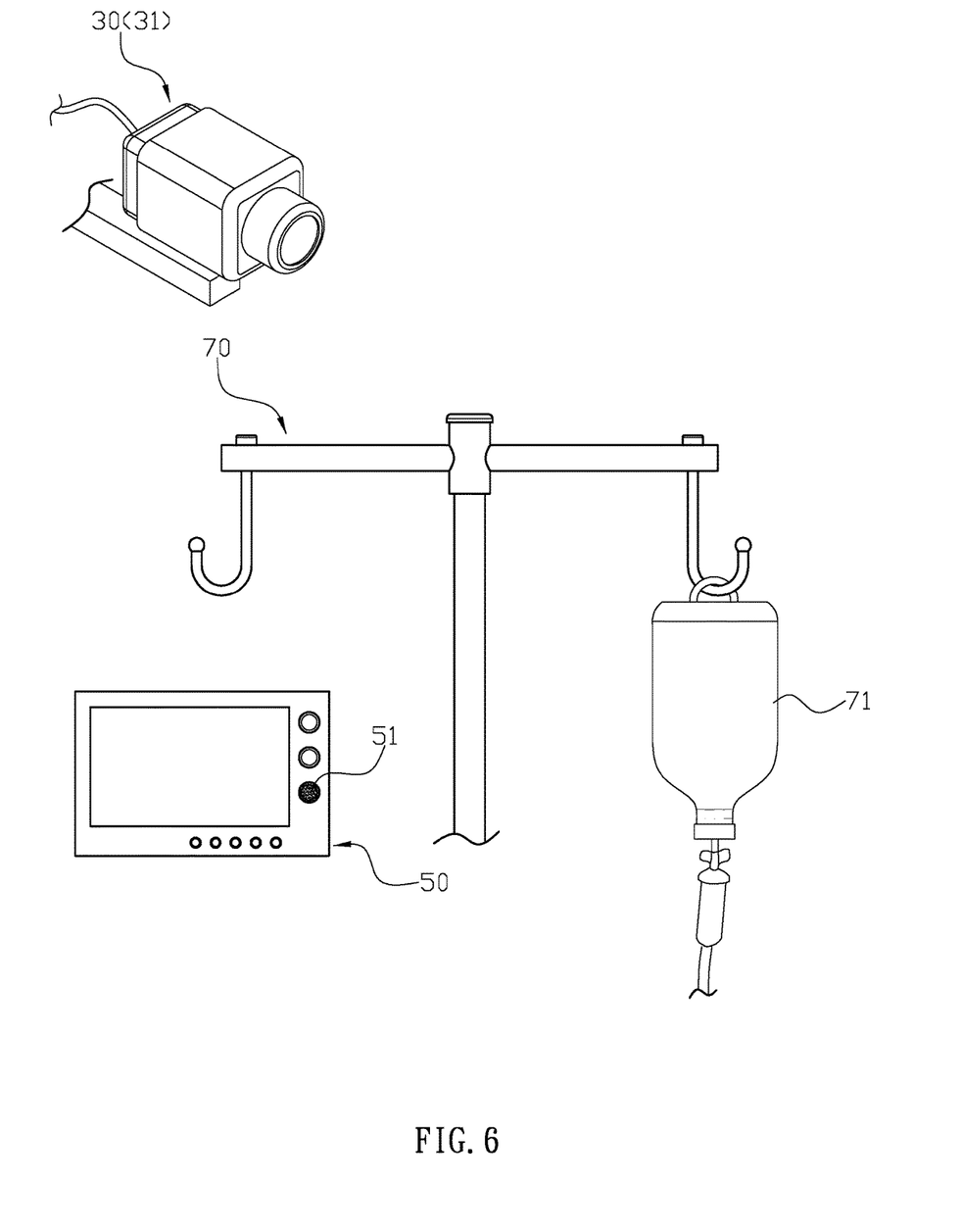
FIG. 6 is a schematic view illustrating the liquid level in the IV bag measured by the second measuring unit of the intelligent hospital bed is at low level in the present invention.

In another particular embodiment, the central processor (50) has three different colors of indicator lights (51) thereon, and the three indicator lights are configured to represent that the liquid level in the IV bag (71) is at high, middle and low level respectively (as shown in FIGS. 4 to 6), so that the caregiver is adapted to monitor the liquid level in the IV bag (71) without the human-computer interaction (80) or looking closely.

In still another particular embodiment, the human-computer interaction (80) is a smart phone, tablet, notebook, laptop or desktop.

In a preferred embodiment, the remote transmission device (60) is configured to send the information to the human-computer interaction (80) through wire transmission.

In another preferred embodiment, the remote transmission device (60) is configured to send the information to the human-computer interaction (80) through wireless transmission.

In still another preferred embodiment, a security camera (90) is installed in a ward around which is configured to surveil around the hospital bed (10), and the security camera (90) is connected to the human-computer interaction (80) held by the patient's family through the remote transmission device (60) such that the patient's family is configured to acquire medical and nursing conditions through instant transmission of the image from the human-computer interaction (80).

Comparing with conventional hospital bed, the present invention is advantageous because: (i) the signals (201)(301)(401) measured from the measuring units (20)(30)(40) are configured to send to central processor (50), and the central processor (50) is adapted to interpret the signals (201)(301)(401) and send the interpreted information to the human-computer interaction (80) through the remote transmission device (60) such that the caregiver is able to master real-time conditions of patients respectively in the hospital beds (10) including injection and urination status at the same time, thereby achieving the most effective allocation and utilization of care resource; and (ii) the caregiver is configured to receive alert from the human-computer interaction (80) when the patient leaves the hospital bed (10) or the intravenous drip of the patient needs to be replaced.

Having described the invention by the description and illustrations above, it should be understood that these are exemplary of the invention and are not to be considered as limiting. Accordingly, the invention is not to be considered as limited by the foregoing description, but includes any equivalents.

What is claimed is:

1. An intelligent hospital bed comprising a hospital bed, a first measuring unit, at least a second measuring unit, a third measuring unit, a central processor and a remote transmission device, wherein the first measuring unit is a pad body having a pressure sensor, and the first measuring unit is installed on the hospital bed; when a patient lies on the hospital bed, the pressure sensor of the first measuring unit is configured to measure the pressure and send a first signal to the central processor which is adapted to determine whether the patient lies on the hospital bed as instructed;

wherein the second measuring unit is an image capturing device adapted to measure the use status of an intravenous bag hanged on an intravenous stand near the hospital bed, and the second measuring unit is adapted to measure the intravenous use status and send a second signal to the central processor which is configured to determine whether the intravenous drip is successful used and to have immediately report for remaining amount of drip in the intravenous bag after each use;

wherein the third measuring unit is a weight measuring device configured to measure the urination condition of the patient and send a third signal to the central processor; and wherein the central processor is configured to receive the signals from the measuring units and interpret the signals through comparison of data in a database of the central processor or a server; after interpreting, the central processor is configured to connect to the remote transmission device and send the interpreted information to a human-computer interaction through the remote transmission device such that a caregiver is able to master real-time conditions of the patient in the hospital bed including injection and urination status at the same time.

2. The intelligent hospital bed of claim 1, wherein the second measuring unit is a camera which is configured for fixed-position photography to determine a liquid level in the intravenous bag.

3. The intelligent hospital bed of claim 1, wherein the second measuring unit is a focal-length-adjustable and optical-zoom camera, and the camera is configured to be timed or manually remote controlled to turn to an designed angle and back so as to monitor a liquid level in the intravenous bag and to monitor around the hospital bed.

4. The intelligent hospital bed of claim 1, wherein the second measuring unit installed on the intravenous stand comprises a crane scale, and the intravenous bag is hung on the crane scale.

5. The intelligent hospital bed of claim 1, wherein the third measuring unit is a weighing platform which enables a urinal pot to be put thereon.

6. The intelligent hospital bed of claim 1, wherein the third measuring unit installed on the hospital bed has a hanging scale to hang a urinal bag thereon.

7. The intelligent hospital bed of claim 1, wherein the central processor has three different colors of indicator lights thereon, and the three indicator lights are configured to represent a liquid level in the intravenous bag is at high, middle and low level respectively.

8. The intelligent hospital bed of claim 1, wherein the human-computer interaction is a smart phone, a tablet, a notebook, a laptop or a desktop.

9. The intelligent hospital bed of claim 1, wherein the remote transmission device is configured to send the information to the human-computer interaction through wire transmission.

10. The intelligent hospital bed of claim 1, wherein the remote transmission device is configured to send the information to the human-computer interaction through wireless transmission.

* * * * *